(12) United States Patent
Matsumura et al.

(10) Patent No.: US 11,737,697 B2
(45) Date of Patent: Aug. 29, 2023

(54) PAD FOR DETECTING BIOPOTENTIALS AND BIOPOTENTIAL DETECTOR

(71) Applicant: NIHON KOHDEN CORPORATION, Tokorozawa (JP)

(72) Inventors: Fumiyuki Matsumura, Tokyo (JP); Norihito Konno, Tokyo (JP); Minori Hosoi, Tokyo (JP); Shigehiro Nishiwaki, Tokyo (JP)

(73) Assignee: Nihon Kohden Corporation, Tokorozawa (JP)

( * ) Notice: Subject to any disclaimer, the term of this patent is extended or adjusted under 35 U.S.C. 154(b) by 1392 days.

(21) Appl. No.: 16/125,128

(22) Filed: Sep. 7, 2018

(65) Prior Publication Data

US 2019/0090770 A1    Mar. 28, 2019

(30) Foreign Application Priority Data

Sep. 28, 2017    (JP) .................... 2017-188541

(51) Int. Cl.
*A61B 5/00* (2006.01)
*H01M 10/44* (2006.01)
*H02J 7/00* (2006.01)
*H02J 50/10* (2016.01)
*A61B 5/25* (2021.01)
(Continued)

(52) U.S. Cl.
CPC .......... *A61B 5/6833* (2013.01); *A61B 5/0006* (2013.01); *A61B 5/25* (2021.01);
(Continued)

(58) Field of Classification Search
CPC ......... A61B 5/25; A61B 5/0006; A61B 5/282; A61B 5/6833; A61B 5/7225;
(Continued)

(56) References Cited

U.S. PATENT DOCUMENTS 8,255,041 B2 *   8/2012   Istvan ............... A61B 5/0006
                                              600/509
2008/0079565 A1   4/2008   Koyama
(Continued)

FOREIGN PATENT DOCUMENTS

JP    H02-049549 U    4/1990
JP    2004121360 A    4/2004
(Continued)

OTHER PUBLICATIONS

English translation of Office Action for JP Application No. 2017-188541, dated May 11, 2021.

*Primary Examiner* — Amine Benlagsir
(74) *Attorney, Agent, or Firm* — Dorsey & Whitney LLP

(57) ABSTRACT

To improve convenience of a biopotential detector. A support includes a lower surface and an upper surface. A first detection electrode is exposed on the lower surface. A first signal terminal is exposed on the upper surface and is electrically connected to the first detection electrode. A secondary battery and a charging circuit are supported in the support. A positive electrode terminal is exposed on the upper surface and is electrically connected to the secondary battery. A gel member covering the first detection electrode is attachable/detachable to/from the lower surface. A signal processing device having a connecting part is attachable/detachable to/from the upper surface. When the signal processing device is attached to the upper surface, the first signal terminal and the positive electrode terminal are connected to the connecting part.

11 Claims, 7 Drawing Sheets

(51) Int. Cl.
    *A61B 5/282*     (2021.01)
    *G06F 3/041*     (2006.01)
    *H01M 10/46*     (2006.01)

(52) U.S. Cl.
    CPC ............ *A61B 5/282* (2021.01); *A61B 5/7225* (2013.01); *G06F 3/041* (2013.01); *H01M 10/44* (2013.01); *H02J 7/0044* (2013.01); *H02J 50/10* (2016.02); *A61B 2560/0214* (2013.01); *A61B 2560/045* (2013.01); *H01M 10/46* (2013.01)

(58) Field of Classification Search
    CPC ...... A61B 2560/0214; A61B 2560/045; G06F 3/041; H01M 10/44; H01M 50/20; H01M 10/46; H02J 7/0044; H02J 7/025; H02J 50/10; Y02E 60/10
    See application file for complete search history.

(56) References Cited

U.S. PATENT DOCUMENTS

| | | | |
|---|---|---|---|
| 2008/0091090 A1* | 4/2008 | Guillory | ............. A61B 5/4094 600/301 |
| 2008/0139953 A1* | 6/2008 | Baker | .................... A61B 5/742 600/509 |
| 2008/0219464 A1* | 9/2008 | Smith | .................... G10K 15/02 381/67 |
| 2011/0228065 A1 | 9/2011 | Koyama | |
| 2012/0157807 A1* | 6/2012 | Virtanen | ................ A61B 5/276 600/372 |
| 2012/0287584 A1 | 11/2012 | Koyama | |
| 2013/0321995 A1 | 12/2013 | Koyama | |
| 2015/0366506 A1 | 12/2015 | Chien et al. | |
| 2016/0183874 A1* | 6/2016 | Takizawa | ............. A61B 5/6832 600/391 |
| 2017/0244436 A1 | 8/2017 | Koyama | |
| 2019/0173505 A1 | 6/2019 | Koyama | |
| 2020/0195286 A1 | 6/2020 | Koyama | |

FOREIGN PATENT DOCUMENTS

| | | |
|---|---|---|
| JP | 200810847 A | 5/2008 |
| JP | 2014100604 A | 6/2014 |
| JP | 2016007525 A | 1/2016 |
| JP | 2016126897 A | 7/2016 |

\* cited by examiner

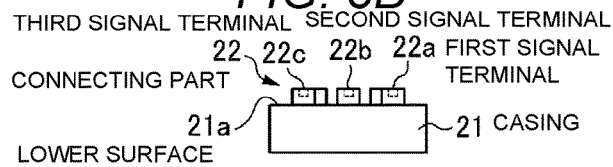
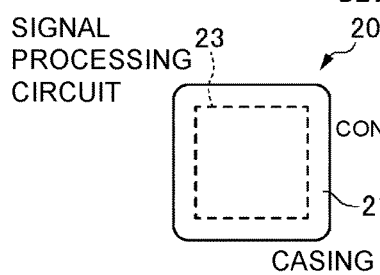
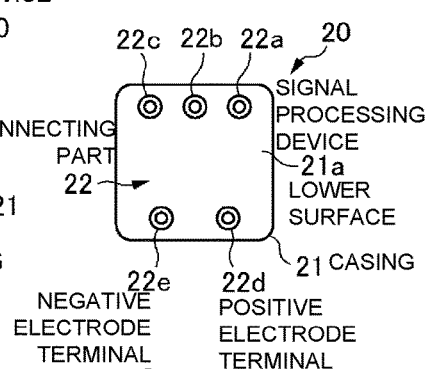
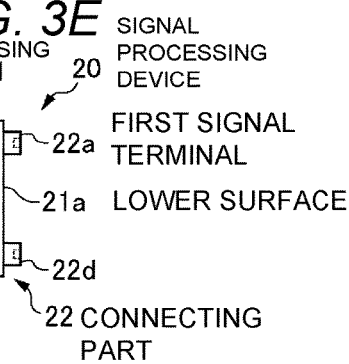
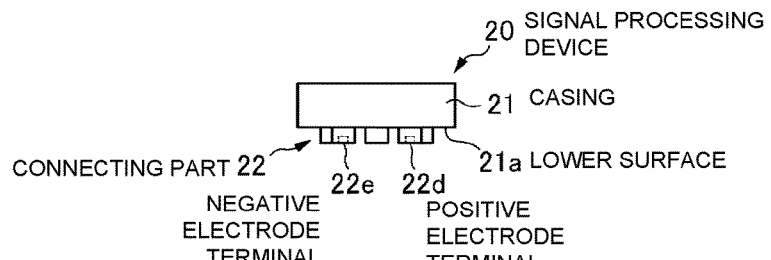
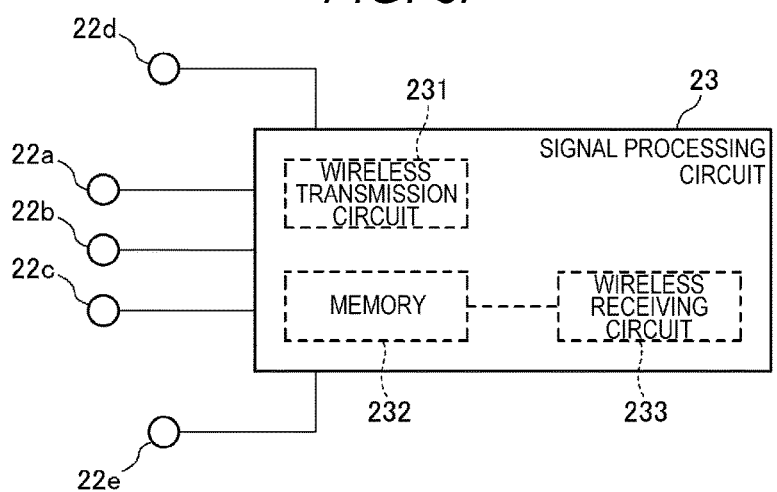

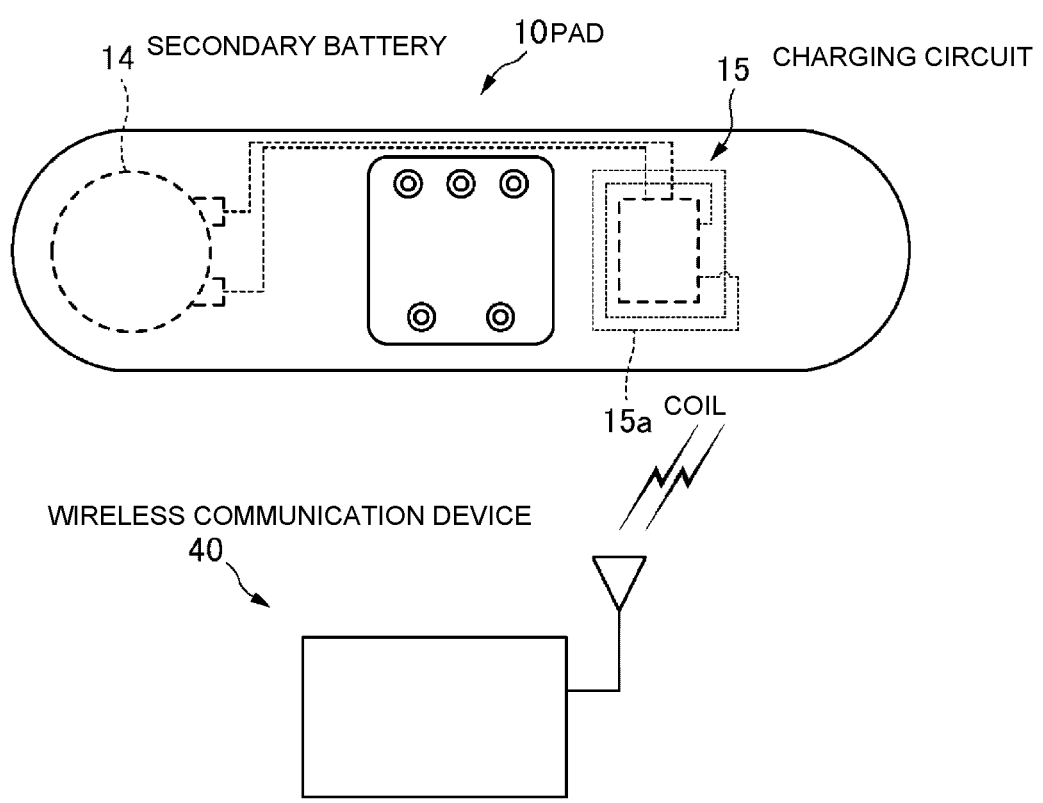

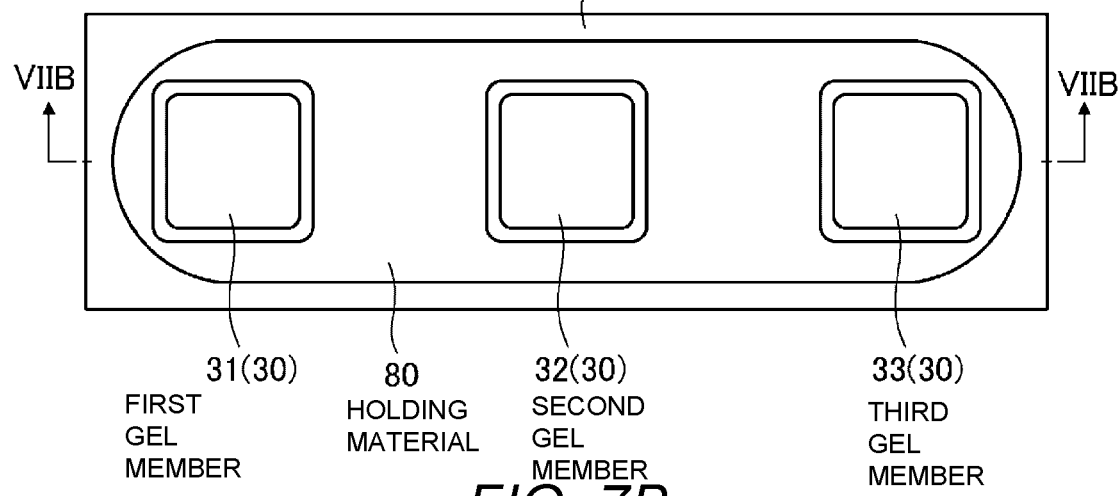
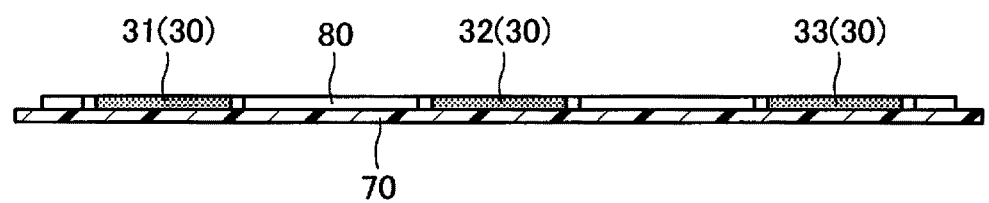
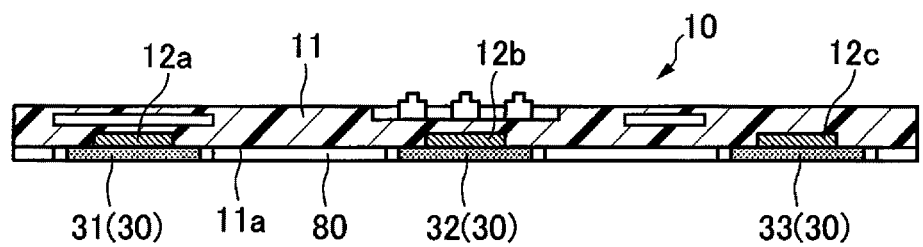

PAD FOR DETECTING BIOPOTENTIALS AND BIOPOTENTIAL DETECTOR

CROSS-REFERENCE TO RELATED APPLICATION(S)

This application claims priority to Japanese Application No. 2017-188541 filed Sep. 28, 2017, which is incorporated herein by reference, in its entirety, for any purpose.

BACKGROUND

1. Field of the Invention

The present invention relates to a pad used for detecting biopotentials and a biopotential detector including the pad.

2. Description of Related Art

A biopotential detector described in JP-A-2004-121360 (Patent Literature 1) includes an electrode pad and a signal processor. The electrode pad has a lower surface and an upper surface. The electrode pad supports electrodes. A gel member having conductivity and adhesiveness is attached to the lower surface of the electrode pad so as to cover the electrodes. Terminals as part of the electrodes are exposed on the upper surface of the electrode pad. The signal processor is attachable/detachable to/from the upper surface of the electrode pad. The signal processor includes a connecting part and a signal processing circuit. When the signal processor is attached to the electrode pad, the terminals are connected to the connecting part. Accordingly, the electrodes and the signal processing circuit are electrically connected through the connecting part.

The electrode pad is attached to a subject so that the lower surface faces the surface of a living body. At this time, the gel member is closely adhered to the surface of the living body (skin). Signals corresponding to biopotentials are taken out from the terminals through the gel member and the electrodes. The signal processing circuit of the signal processor performs processing for wirelessly transmitting the signals. Power for performing signal processing is supplied from a battery built in the signal processor.

SUMMARY OF THE INVENTION

An object of the present invention is to improve convenience of the biopotential detector such as one described above.

A pad for detecting biopotentials according to an embodiment of the present invention includes a support having a first surface and a second surface, electrodes exposed on the first surface, first terminals exposed on the second surface and electrically connected to the electrodes, a secondary battery supported in the support, a charging circuit supported in the support and for charging the secondary battery, and second terminals exposed on the second surface and electrically connected to the secondary battery, in which gel members covering the electrodes are attachable/detachable to/from the first surface, a signal processing device having a connecting part is attachable/detachable to/from the second surface, and when the signal processing device is attached to the second surface, the first terminals and the second terminals are connected to the connecting part.

A biopotential detector according to an embodiment of the present invention includes a first support having a first surface and a second surface, first electrodes exposed on the first surface, first terminals exposed on the second surface and electrically connected to the first electrodes, a secondary battery supported in the first support, a charging circuit supported in the first support and for charging the secondary battery, second terminals exposed on the second surface and electrically connected to the secondary battery, gel members that are attachable/detachable to/from the first surface so as to cover the first electrodes and a signal processing device that is attachable/detachable to/from the second surface, in which the signal processing device has a connecting part connected to the first terminals and the second terminals, and a signal processing circuit that processes biopotential signals inputted from the connection part.

In the above respective examples, the signal processing device and the gel members are attachable/detachable to/from the support of the pad for detecting biopotentials in which the rechargeable secondary battery is supported. According to the structure, the convenience of the biopotential detector can be improved due to reasons explained below.

First, it is not necessary to provide an internal power supply for driving the signal processing circuit inside the signal processing device, therefore, the signal processing device can be reduced in size and weight. Accordingly, the center of gravity in the biopotential detector comes close to the body of the subject and it becomes easy to hold the biopotential detector on the skin of the subject. That is, the adhesive area of the gel member can be reduced more when the same holding force is obtained, therefore, material costs can be reduced. Adhesive duration can be extended when the gel member having the same adhesive force is used.

Secondly, the pad for detecting biopotentials can be reused. As it is only necessary to replace the gel member with a lower product unit price at each measurement, an operation cost of the biopotential detector can be reduced while meeting the requirements on sanitation.

Thirdly, it is possible to replace only the pad for detecting biopotentials at suitable timing by dividing parts which can be reused between the signal processing device having a relatively long product lifetime and the pad for detecting biopotentials having a relatively short product lifetime. For example, when the secondary battery is charged and discharged repeatedly for reusing the pad, battery performance is gradually deteriorated. In such case, the signal processing device having a relatively long product lifetime and a high product unit price can be continuously reused by replacing only the pad. Also according to this, the operation cost of the biopotential detector can be reduced.

BRIEF DESCRIPTION OF THE DRAWINGS

FIGS. 3A to 3F show a structure of a signal processing device in the above biopotential detector;

FIG. 4 is a view for explaining wireless charging of the above biopotential detector;

FIGS. 7A to 7C show another example of the sheet in FIG. 6.

DETAILED DESCRIPTION

Figure 1A:
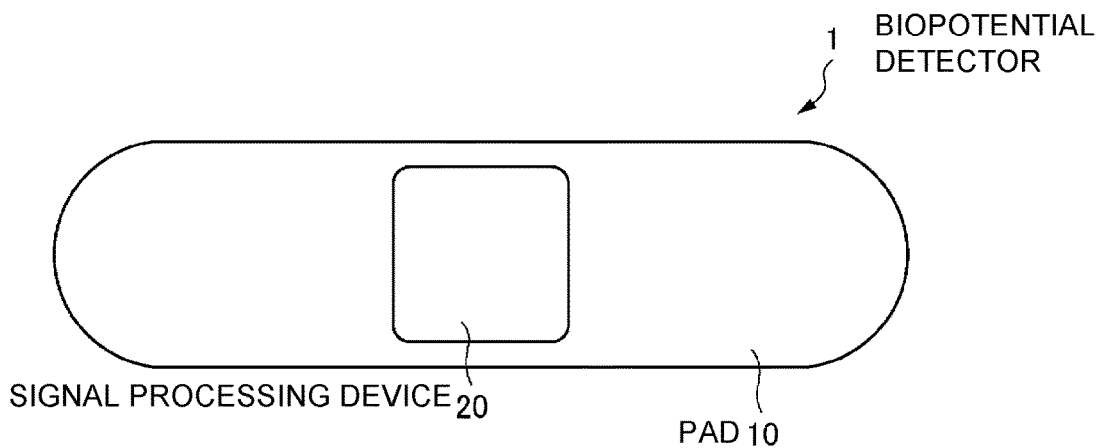
FIGS. 1A to 1C show a structure of a biopotential detector according to an embodiment.
Figure 1B:
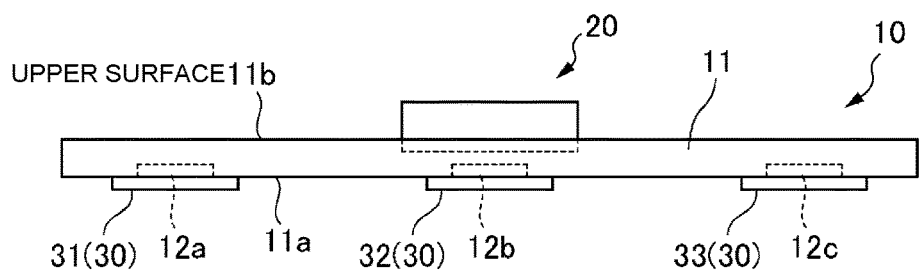
Figure 1C:
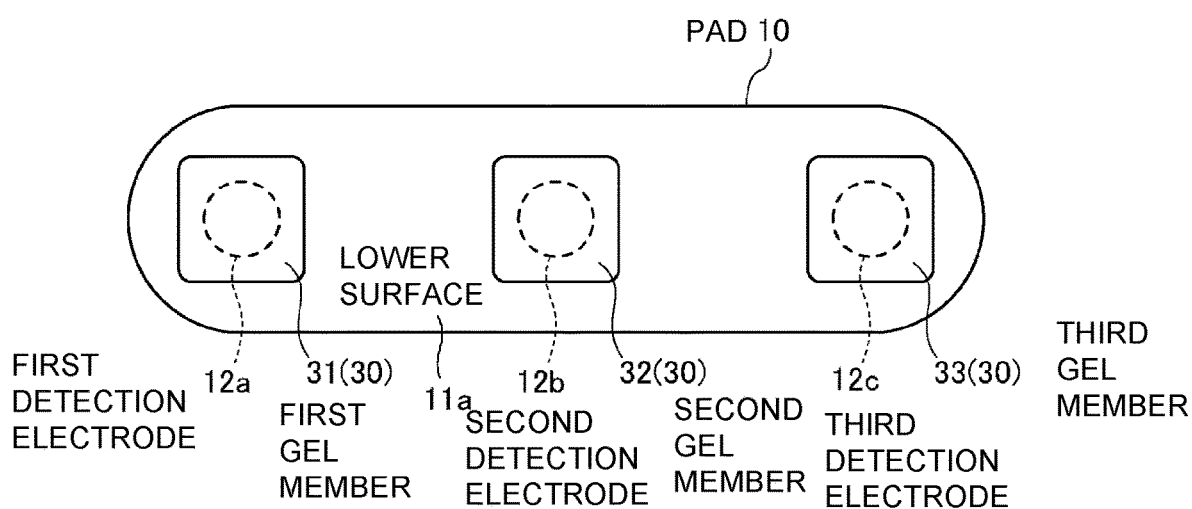

Hereinafter, embodiments will be explained in detail with reference to the attached drawings. FIG. 1A shows an external appearance of a biopotential detector 1 according to an embodiment seen from above. FIG. 1B shows an external appearance of the biopotential detector 1 seen from the front. FIG. 1C shows an external appearance of the biopotential detector 1 seen from below. Expressions such as "above", "below", "front", "rear", "left" and "right" used in the specification are just used for convenience for explaining structures, which are not intended to limit postures of the biopotential detector 1 at the time of use.

The biopotential detector 1 according to the embodiment is used for measuring an electrocardiogram of a subject. The biopotential detector 1 includes a pad 10, a signal processing device 20 and a gel member 30.

The pad 10 has a support 11. The support 11 includes a lower surface 11a and an upper surface 11b. The support 11 is an example of a first support. The lower surface 11a is an example of a first surface. The upper surface 11b is an example of a second surface.

The pad 10 has a first detection electrode 12a, a second detection electrode 12b and a third detection electrode 12c. The first detection electrode 12a, the second detection electrode 12b and the third detection electrode 12c are exposed on the lower surface 11a of the support 11. The first detection electrode 12a, the second detection electrode 12b and the third detection electrode 12c have conductivity. The first detection electrode 12a, the second detection electrode 12b and the third detection electrode 12c are examples of first electrodes.

The gel member 30 includes a first gel member 31, a second gel member 32 and a third gel member 33. The first gel member 31, the second gel member 32 and the third gel member 33 have adhesiveness and conductivity.

The first gel member 31 is arranged on the lower surface 11a of the support 11 so as to cover the first detection electrode 12a. The first gel member 31 is attached to the lower surface 11a so as to be peeled off.

The second gel member 32 is arranged on the lower surface 11a of the support 11 so as to cover the second detection electrode 12b. The second gel member 32 is attached to the lower surface 11a so as to be peeled off.

The third gel member 33 is arranged on the lower surface 11a of the support 11 so as to cover the third detection electrode 12c. The third gel member 33 is attached to the lower surface 11a so as to be peeled off.

The signal processing device 20 is arranged on the upper surface 11b of the support 11. The signal processing device 20 is attached to the upper surface 11b so as to be detached.

Figure 2A:
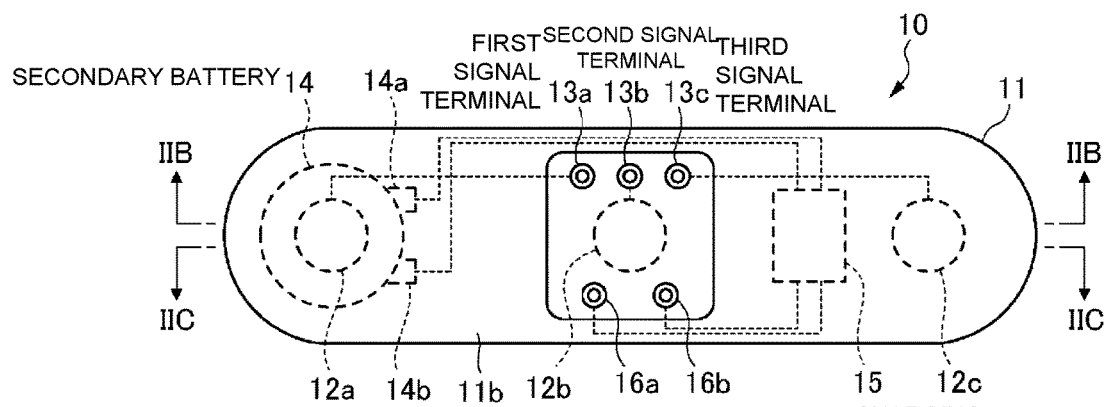
FIGS. 2A to 2D show a structure of a pad in the above biopotential detector.
Figure 2B:
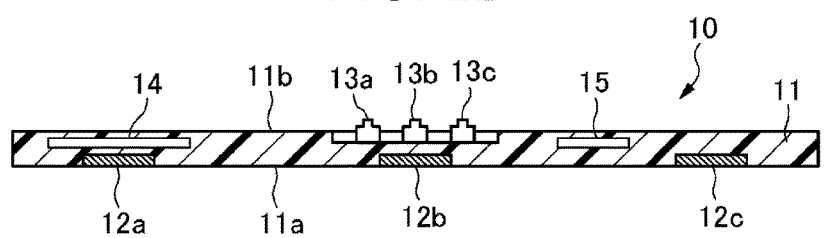
Figure 2C:
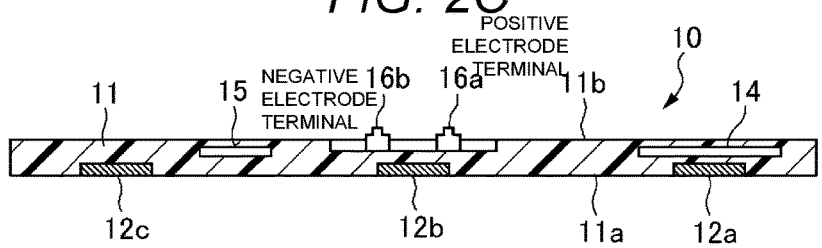
Figure 2D:
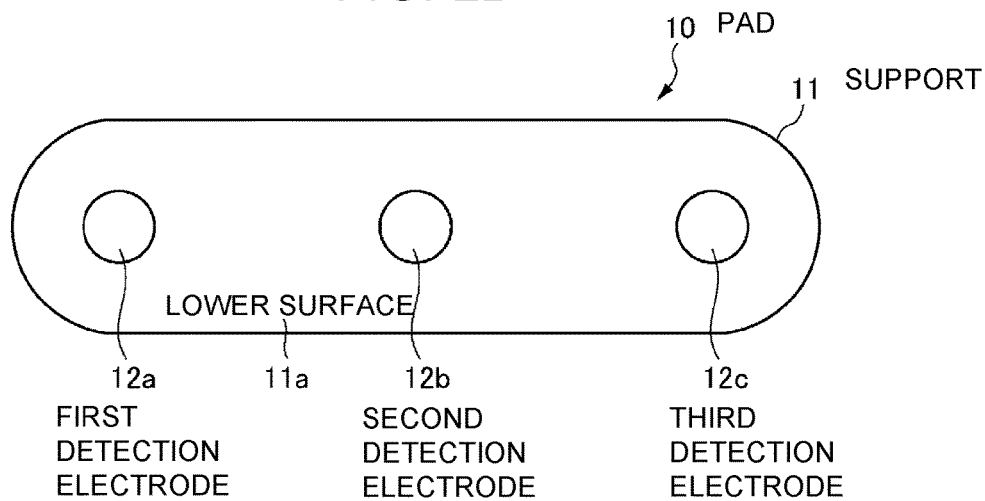

FIG. 2A shows an external appearance of the pad 10 seen from above. FIG. 2B shows a structure of a cross section taken along a line IIB-IIB in FIG. 2A from an arrow direction. FIG. 2C shows a structure of a cross section taken along a line IIC-IIC in FIG. 2A from an arrow direction. FIG. 2D shows an external appearance of the pad 10 seen from below.

The pad 10 includes a first signal terminal 13a, a second signal terminal 13b and a third signal terminal 13c. The first signal terminal 13a, the second signal terminal 13b and the third signal terminal 13c are exposed on the upper surface 11b of the support 11. The first signal terminal 13a, the second signal terminal 13b and the third signal terminal 13c have conductivity. The first signal terminal 13a, the second signal terminal 13b and the third signal terminal 13c are examples of first terminals.

An expression of "electrically connected" used in the following explanation has two meanings including direct connection and indirect connection if a conductive state is achieved between the both.

The first signal terminal 13a is electrically connected to the first detection electrode 12a through wiring provided inside the support 11. The wiring is not shown in FIG. 2B and FIG. 2C.

The second signal terminal 13b is electrically connected to the second detection electrode 12b through wiring provided inside the support 11. The wiring is not shown in FIG. 2B and FIG. 2C.

The third signal terminal 13c is electrically connected to the third detection electrode 12c through wiring provided inside the support 11. The wiring is not shown in FIG. 2B and FIG. 2C.

The pad 10 is provided with a secondary battery 14. The secondary battery 14 is supported inside the support 11. The secondary battery 14 has a positive electrode terminal 14a and a negative electrode terminal 14b. As examples of the secondary battery 14, a lithium-ion battery, a Nickel-Cadmium battery and a manganese-dioxide lithium battery can be cited.

The pad 10 is provided with a charging circuit 15. The charging circuit 15 is supported inside the support 11. The charging circuit 15 is electrically connected to the secondary battery 14 through wiring provided inside the support 11. The wiring is not shown in FIG. 2B and FIG. 2C.

The pad 10 includes a positive electrode terminal 16a and a negative electrode terminal 16b. The positive electrode terminal 16a and the negative electrode terminal 16b are exposed on the upper surface 11b of the support 11. The positive electrode terminal 16a and the negative electrode terminal 16b have conductivity. The positive electrode terminal 16a and the negative electrode terminal 16b are examples of second terminals.

The positive electrode terminal 16a is electrically connected to the positive electrode terminal 14a of the secondary battery 14 through wiring provided inside the support 11 and the charging circuit 15. The wiring is not shown in FIG. 2B and FIG. 2C.

The negative electrode terminal 16b is electrically connected to the negative electrode terminal 14b of the secondary battery 14 through wiring provided inside the support 11 and the charging circuit 15. The wiring is not shown in FIG. 2B and FIG. 2C.

The charging circuit 15 has a function of charging the battery by allowing electric current to flow in the secondary battery 14. The charging circuit 15 also has a function of supplying power generated by the secondary battery 14 to the positive electrode terminal 16a and the negative electrode terminal 16b. The charging circuit 15 further has a function of shutting off the power supply to the positive electrode terminal 16a and the negative electrode terminal 16b when an output voltage from the secondary battery 14 becomes less than a predetermined value. As these functions of the charging circuit 15 are well known, detailed explanation is omitted.

FIG. 3A shows an external appearance of the signal processing device 20 seen from above. FIG. 3B shows an external appearance of the signal processing device 20 seen from the rear. FIG. 3C shows an external appearance of the signal processing device 20 seen from below. FIG. 3D shows an external appearance of the signal processing device 20 seen from the front. FIG. 3E shows an external appearance of the signal processing device 20 seen from right. An external appearance of the signal processing device 20 seen from left is not shown as that is a symmetry of one shown in FIG. 3E.

The signal processing device 20 has a casing 21. The signal processing device 20 has a connecting part 22 on a lower surface 21a of the casing 21.

The connecting part 22 includes a first signal terminal 22a, a second signal terminal 22b, a third signal terminal 22c, a positive electrode terminal 22d and a negative electrode terminal 22e. The first signal terminal 22a, the second signal terminal 22b, the third signal terminal 22c, the positive electrode terminal 22d and the negative electrode terminal 22e have conductivity.

As shown in FIG. 3A, the signal processing device 20 is provided with a signal processing circuit 23. The signal processing circuit 23 is housed inside the casing 21.

As shown in FIG. 3F, the signal processing circuit 23 is electrically connected to the first signal terminal 22a, a second signal terminal 22b, the third signal terminal 22c, the positive electrode terminal 22d and the negative electrode terminal 22e.

As shown in FIG. 1B, the signal processing device 20 is attached to the pad 10 in a posture in which the lower surface 21a of the casing 21 faces the upper surface 11b of the support 11.

As shown in FIG. 2B, the first signal terminal 13a of the pad 10 has a convex portion. On the other hand, the first signal terminal 22a of the signal processing device 20 has a concave portion as shown in FIG. 3B and FIG. 3C. When the signal processing device 20 is attached to the pad 10, the convex portion is fitted to the concave portion to thereby connect the first signal terminal 13a and the first signal terminal 22a.

As shown in FIG. 2B, the second signal terminal 13b of the pad 10 has a convex portion. On the other hand, the second signal terminal 22b of the signal processing device 20 has a concave portion as shown in FIG. 3B and FIG. 3C. When the signal processing device 20 is attached to the pad 10, the convex portion is fitted to the concave portion to thereby connect the second signal terminal 13b and the second signal terminal 22b.

As shown in FIG. 2B, the third signal terminal 13c of the pad 10 has a convex portion. On the other hand, the third signal terminal 22c of the signal processing device 20 has a concave portion as shown in FIG. 3B and FIG. 3C. When the signal processing device 20 is attached to the pad 10, the convex portion is fitted to the concave portion to thereby connect the third signal terminal 13c and the third signal terminal 22c.

As shown in FIG. 2C, the positive electrode terminal 16a of the pad 10 has a convex portion. On the other hand, the positive electrode terminal 22d of the signal processing device 20 has a concave portion as shown in FIG. 3C and FIG. 3D. When the signal processing device 20 is attached to the pad 10, the convex portion is fitted to the concave portion to thereby connect the positive electrode terminal 16a and the positive electrode terminal 22d.

As shown in FIG. 2C, the negative electrode terminal 16b of the pad 10 has a convex portion. On the other hand, the negative electrode terminal 22e of the signal processing device 20 has a concave portion as shown in FIG. 3C and FIG. 3D. When the signal processing device 20 is attached to the pad 10, the convex portion is fitted to the concave portion to thereby connect the negative electrode terminal 16b and the negative electrode terminal 22e.

According to the above, the positive electrode terminal 14a of the secondary battery 14 is electrically connected to the positive electrode terminal 22d of the signal processing device 20. Similarly, the negative electrode terminal 14b of the secondary battery 14 is electrically connected to the negative electrode terminal 22e of the signal processing device 20. Therefore, the signal processing circuit 23 is driven by power supplied from the secondary battery 14. That is, the signal processing device 20 is not provided with a power supply for driving the signal processing circuit 23 thereinside.

When the biopotential detector 1 is arranged at a given position in a body of the subject, the biopotential detector 1 is held on the skin due to the adhesiveness of the gel member 30. As the gel member 30 has conductivity, biopotentials of corresponding body portions are detected respectively at the first detection electrode 12a, the second detection electrode 12b and the third detection electrode 12c of the pad 10.

A first biopotential signal corresponding to a biopotential detected by the first detection electrode 12a is inputted into the signal processing circuit 23 through the first signal terminal 13a of the pad 10 and the first signal terminal 22a of the signal processing device 20.

A second biopotential signal corresponding to a biopotential detected by the second detection electrode 12b is inputted into the signal processing circuit 23 through the second signal terminal 13b of the pad 10 and the second signal terminal 22b of the signal processing device 20.

A third biopotential signal corresponding to a biopotential detected by the third detection electrode 12c is inputted into the signal processing circuit 23 through the third signal terminal 13c of the pad 10 and the third signal terminal 22c of the signal processing device 20.

The signal processing circuit 23 performs processing of acquiring electrocardiogram information based on the first biopotential signal, the second biopotential signal and the third biopotential signal inputted through the first signal terminal 22a, the second signal terminal 22b and the third signal terminal 22c.

Specifically, first electrocardiogram information based on the lead obtained between the first detection electrode 12a and the second detection electrode 12b can be obtained by using the second detection electrode 12b as an indifferent electrode. Similarly, second electrocardiogram information based on the lead obtained between the second detection electrode 12b and the third detection electrode 12c can be obtained.

When the measurement is completed, the signal processing device 20 and the gel member 30 are removed from the pad 10. The gel member 30 is discarded. The secondary battery 14 of the pad 10 is recharged according to need.

Figure 6A:
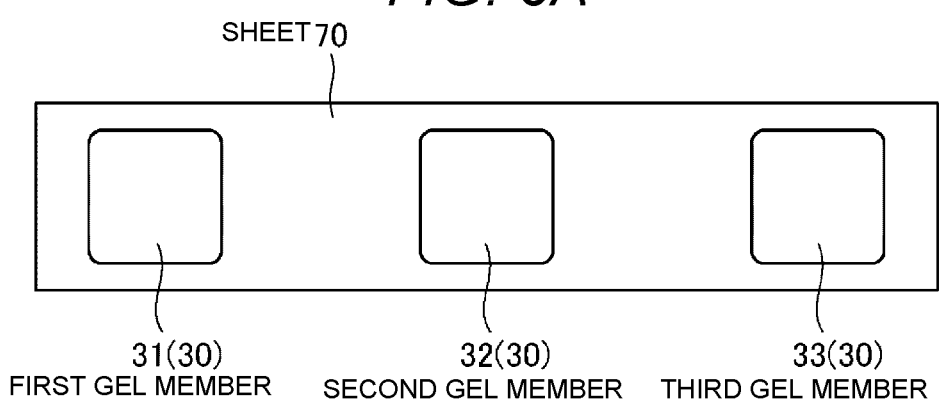
FIGS. 6A and 6B show a sheet supporting gel members attached to the pad in FIG. 2.
Figure 6B:
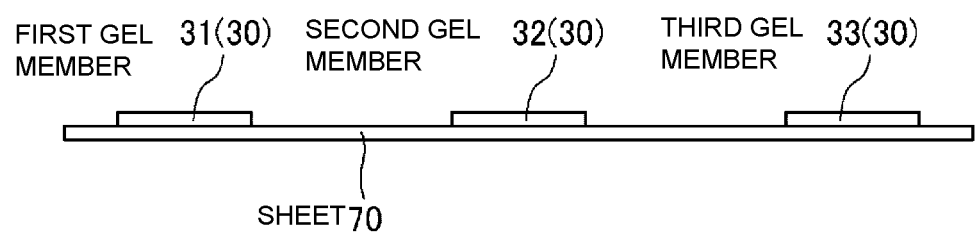

FIG. 6A shows an external appearance of a state in which the gel member 30 for replacement is supported on a sheet 70 seen from above. FIG. 6B shows an external appearance of the same state seen from the front. The arrangement of the first gel member 31, the second gel member 32 and the third gel member 33 on the sheet 70 corresponds to positions of the first detection electrode 12a, the second detection electrode 12b and the third detection electrode 12c on the lower surface 11a of the pad 10. The gel member 30 is covered with a protective sheet (not shown) which can be peeled off.

At the time of next measurement, the protective sheet is peeled off to expose the gel member 30. When the pad 10 is placed on the exposed gel member 30, the gel member 30 is adhered to the lower surface 11a of the support 11. As the sheet 70 is peeled off lastly, the state shown in FIGS. 1B and 1C can be obtained. The sheet 70 is discarded.

As shown in FIG. 7A, the sheet 70 may support a holding material 80 in addition to the gel member 30. FIG. 7B shows a structure of a cross section taken alone a line VIIB-VIIB in FIG. 7A from an arrow direction. The holding material 80 has adhesiveness at least on a surface facing the lower surface 11a of the support 11 and a surface to be adhered to the subject (namely, a surface contacting the sheet 70). The holding material 80 is formed of, for example, a felt material, a foaming material, a silicone material, a urethane material, an elastomeric material or the like on which the above adhesive layers are provided. The holding material 80 may be entirely formed of a gel material, a hydrocolloid material or the like having adhesiveness. The holding material 80 is covered with a protective sheet (not shown) which can be peeled off together with the gel member 30.

At the time of use, the protective sheet is peeled off to expose the gel member 30 and the holding material 80. When the pad 10 is placed on the exposed gel member 30 and the holding material 80, the gel member 30 and the holding material 80 are adhered to the lower surface 11a of the support 11. As the sheet 70 is peeled off lastly, a state shown in FIG. 7C can be obtained. The same drawing shows a cross section corresponding to FIG. 2B. As the adhesiveness of the holding member 80 is added, a holding force of the biopotential detector 1 with respect to the body of the subject is increased.

As described above, in the biopotential detector 1 according to the embodiment, the signal processing device 20 and the gel member 30 are attachable/detachable to/from the pad 10 that is provided with the rechargeable secondary battery 14. According to the structure, the convenience of the biopotential detector 1 can be improved due to reasons explained below.

First, it is not necessary to provide an internal power supply for driving the signal processing circuit 23 inside the signal processing device 20, therefore, the signal processing device 20 can be reduced in size and weight. Accordingly, the center of gravity in the biopotential detector 1 comes close to the body of the subject and it becomes easy to hold the biopotential detector 1 on the skin of the subject. That is, the adhesive area of the gel member 30 can be reduced more when the same holding force is obtained, therefore, material costs can be reduced. Adhesive duration can be extended when the gel member 30 having the same adhesive force is used.

Secondly, the pad 10 can be reused. As it is only necessary to replace the gel member 30 with a lower product unit price at each measurement, an operation cost of the biopotential detector 1 can be reduced while meeting the requirements on sanitation.

Thirdly, it is possible to replace only the pad 10 at suitable timing by dividing parts which can be reused between the signal processing device 20 having a relatively long product lifetime and the pad 10 having a relatively short product lifetime. For example, when the secondary battery 14 is charged and discharged repeatedly for reusing the pad 10, battery performance is gradually deteriorated. In such case, the signal processing device 20 having a relatively long product lifetime and a high product unit price can be continuously reused by replacing only the pad 10. Also according to this, the operation cost of the biopotential detector 1 can be reduced.

As shown in FIG. 4, the secondary battery 14 and the charging circuit 15 of the pad 10 is configured so as to be wirelessly charged in the embodiment. Specifically, the charging circuit 15 includes a coil 15a. The wireless communication device 40 also has a coil. When electromagnetic induction is caused between both coils, power is generated in the charging circuit 15. Electric current flowing by the generated power is supplied to the secondary battery 14.

According to the above structure, a user is released from troublesomeness of wiring or connection and the secondary battery 14 can be charged efficiently. It is also possible to charge plural secondary batteries 14 all at once by arranging plural pads 10 near a wireless communication device 40. Accordingly, the convenience of the biopotential detector 1 can be improved.

As shown in FIG. 3F, the signal processing circuit 23 according to the embodiment includes a wireless transmission circuit 231. The wireless transmission circuit 231 wirelessly transmits data corresponding to electrocardiogram information acquired by the signal processing circuit 23 to a remote external device (not shown). As examples of the remote external device, an arithmetic device, a display device and so on can be cited.

It is also preferable that data corresponding to biopotential signals inputted from the connecting part 22 is wirelessly transmitted without performing processing of acquiring electrocardiogram information by the signal processing circuit 23. In this case, the signal processing circuit 23 performs processing of converting the biopotential signals into data in a format suitable for wireless transmission. The electrocardiogram information is acquired by the remote external device which has acquired the data.

According to the above structure, the action of the subject wearing the biopotential detector 1 is not restricted due to wiring and so on. Therefore, the convenience of the biopotential detector 1 can be improved.

The signal processing circuit 23 may include a memory 232 in addition to or instead of the above structure. The memory 232 stores data corresponding to the biopotential signals inputted from the connecting part 22. Data stored in the memory 232 is read out from the signal processing device 20 removed from the pad after the measurement is finished through wired communication or wireless communication to be subjected to necessary processing. The memory 232 may be a portable memory attachable/detachable to/from the casing 21. In that case, necessary data is directly read from the memory 232.

According to the above structure, data corresponding to the biopotential signals acquired by the subject can be used at desired timing. Therefore, the action of the subject wearing the biopotential detector 1 is not restricted within a communicable range with respect to the remote external device. Therefore, the convenience of the biopotential detector 1 can be improved.

The memory 232 may store information for specifying the subject in addition to or instead of the above structure. The information can be read at any time by, for example, the wireless communication device 40. The information may be associated with biopotential signals inputted from the connecting part 22.

According to the above structure, a specific signal processing device 20 can be associated with a specific subject. Therefore, occurrence of a situation in which acquired data is wrongly handled as data of another subject can be suppressed. Therefore, the convenience of the biopotential device 1 can be improved. In a case where the acquired data is stored in the memory 232 once and handled in a state of being separated from the pad 10, the above structure is particularly effective.

Information for specifying the subject may be written in the memory 232 through wired communication or wireless communication. The latter is more preferable from the viewpoint of convenience. In this case, the signal processing circuit 23 may include a wireless receiving circuit 233 as shown in FIG. 3F. The wireless receiving circuit 23 receives information for specifying the subject, for example, through the wireless communication device 40 shown in FIG. 4.

Information received by the wireless receiving circuit 233 is converted into information in a suitable data format and stored in the memory 232.

Figure 5A:
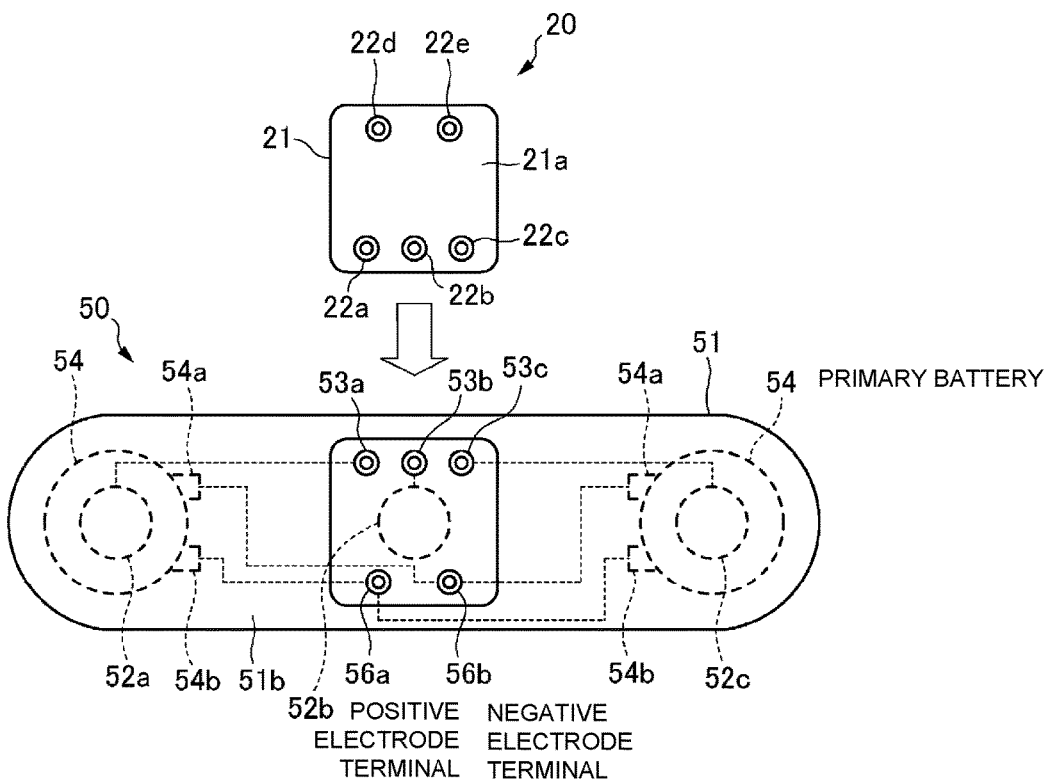
FIGS. 5A and 5B show another example of a pad used for the above biopotential detector.
Figure 5B:
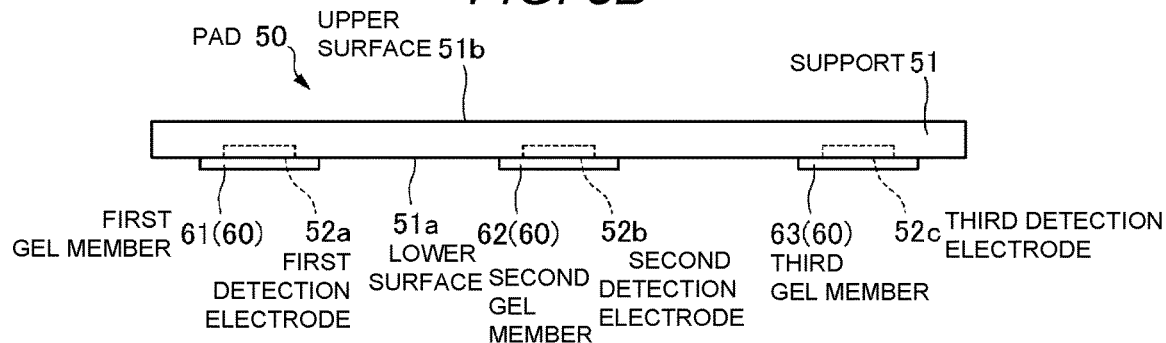

FIG. 5A shows a structure of a pad 50 according to another example seen from above. FIG. 5B shows an external appearance of the pad 50 seen from the front.

The pad 50 supports a support 51. The support 51 has a lower surface 51a and an upper surface 51b. The support 51 is an example of a second support. The lower surface 51a is an example of a third surface. The upper surface 51b is an example of a fourth surface.

The pad 50 has a first detection electrode 52a, a second detection electrode 52b and a third detection electrode 52c. The first detection electrode 52a, the second detection electrode 52b and the third detection electrode 52c have conductivity. The first detection electrode 52a, the second detection electrode 52b and the third detection electrode 52c are examples of second electrodes.

The pad 50 has a gel member 60. The gel member 60 includes a first gel member 61, a second gel member 62 and a third gel member 63. The first gel member 61, the second gel member 62 and the third gel member 63 have adhesiveness and conductivity.

The first gel member 61 covers the first detection electrode 52a on the lower surface 51a of the support 51. The first gel member 61 is not capable of being peeled off from the lower surface 51a.

The second gel member 62 covers the second detection electrode 52b on the lower surface 51a of the support 51. The second gel member 62 is not capable of being peeled off from the lower surface 51a.

The third gel member 63 covers the third detection electrode 52c on the lower surface 51a of the support 51. The third gel member 63 is not capable of being peeled off from the lower surface 51a.

The pad 50 includes a first signal terminal 53a, a second signal terminal 53b and a third signal terminal 53c. The first signal terminal 53a, the second signal terminal 53b and the third signal terminal 53c are exposed on the upper surface 51b of the support 51. The first signal terminal 53a, the second signal terminal 53b and the third signal terminal 53c have conductivity. The first signal terminal 53a, the second signal terminal 53b and the third signal terminal 53c are examples of fifth terminals.

The first signal terminal 53a is electrically connected to the first detection electrode 52a through wiring provided inside the support 51.

The second signal terminal 53b is electrically connected to the second detection electrode 52b through wiring provided inside the support 51.

The third signal terminal 53c is electrically connected to the third detection electrode 52c through wiring provided inside the support 51.

The pad 50 is provided with a primary battery 54. As examples of the primary battery 54, a lithium coin battery, an air-zinc battery and an alkaline button battery can be cited. The primary battery 54 is supported inside the support 51. The primary battery 54 has a positive electrode terminal 54a and a negative electrode terminal 54b.

The pad 50 includes a positive electrode terminal 56a and a negative electrode terminal 56b. The positive electrode terminal 56a and the negative electrode terminal 56b are exposed on the upper surface 51b of the support 51. The positive electrode terminal 56a and the negative electrode terminal 56a and the negative electrode terminal 56b have conductivity. The positive electrode terminal 56a and the negative electrode terminal 56b are examples of sixth terminals.

The positive electrode terminal 56a is electrically connected to the positive electrode terminal 54a of the primary battery 54 through wiring provided inside the support 51.

The negative electrode terminal 56b is electrically connected to the negative electrode terminal 54b of the secondary battery 54 through wiring provided inside the support 51.

As shown in FIG. 5A, the signal processing device 20 is attached to the pad 50 in a posture in which the lower surface 21a of the casing 21 faces the upper surface 51b of the support 51.

When the signal processing device 20 is attached to the pad 50, the first signal terminal 53a of the pad 50 and the first signal terminal 22a of the signal processing device 20 are connected.

Similarly, the second signal terminal 53b of the pad 50 and the second signal terminal 22b of the signal processing device 20 are connected, and the third signal terminal 53c of the pad 50 and the third signal terminal 22c of the signal processing device 20 are connected.

Similarly, the positive electrode terminal 56a of the pad 50 and the positive electrode terminal 22d of the signal processing device 20 are connected, and the negative electrode terminal 56b of the pad 50 and the negative electrode terminal 22e of the signal processing device 20 are connected.

Accordingly, the positive electrode terminal 54a of the primary battery 54 is electrically connected to the positive electrode terminal 22d of the signal processing device 20. Similarly, the negative electrode terminal 54b of the primary battery 54 is electrically connected to the negative electrode terminal 22e of the signal processing device 20. Therefore, the signal processing circuit 23 is driven by power supplied from the primary battery 54.

A first biopotential signal corresponding to a biopotential detected by the first detection electrode 52a is inputted into the signal processing circuit 23 through the first signal terminal 53a of the pad 50 and the first signal terminal 22a of the signal processing device 20.

A second biopotential signal corresponding to a biopotential detected by the second detection electrode 52b is inputted into the signal processing circuit 23 through the second signal terminal 53b of the pad 50 and the second signal terminal 22b of the signal processing device 20.

A third biopotential signal corresponding to a biopotential detected by the third detection electrode 52c is inputted into the signal processing circuit 23 through the third signal terminal 53c of the pad 50 and the third signal terminal 22c of the signal processing device 20.

When the measurement is completed, the signal processing device 20 is removed from the pad 50. The pad 50 and the gel member 60 are discarded.

According to the above structure, the signal processing device 20 can be used in common between the pad 50 which does not require recharging though the product unit price is relatively high and the pad 10 which can reduce the operation cost by being reused, and the pads can be properly used according to need. Therefore, the convenience of the biopotential detector 1 is improved.

The above embodiments are just exemplifications for making the present invention easy to understand. The structures according to the above embodiments may be altered and modified within a scope not departing from the gist of the present invention.

In the above embodiment, the secondary battery 14 is charged through the charging circuit 15 by wireless charging through the wireless communication device 40. However, it is also possible that charging is performed by providing a suitable power feeding terminal in the pad 10 and connecting the power feeding terminal to a charging device such as a cradle.

In the above embodiment, the terminals provided in the pad 10 have convex portions and the terminals provided in the signal processing device 20 have concave portions. However, a structure in which terminals provided in the pad 10 have concave portions and terminals provided in the signal processing device 20 have convex portions may be also adopted. The same applies to the pad 50.

In the above embodiment, the first signal terminal 13a, the second signal terminal 13b, the third signal terminal 13c, the positive electrode terminal 16a and the negative electrode terminal 16b of the pad 10 are plural terminals which are independently exposed. However, these terminals may be arranged in a common connector housing. It is also possible to provide a connector housing which houses the first signal terminal 13a, the second signal terminal 13b and the third signal terminal 13c, and a connector housing which houses the positive electrode terminal 16a and the negative electrode housing 16b.

Similarly, the first detection electrode 52a, the second detection electrode 52b, the third detection electrode 52c, the positive electrode terminal 56a and the negative electrode terminal 56b of the pad 50 are plural terminals which are independently exposed. However, these terminals may be arranged in a common connector housing. It is also possible to provide a connector housing which houses the first detection terminal 52a, the second detection terminal 52b and the third detection terminal 52c, and a connector housing which houses the positive electrode terminal 56a and the negative electrode housing 56b.

In this case, the connecting part 22 of the signal processing device 20 may take a form of a common connector housing which houses the first signal terminal 22a, the second signal terminal 22b, the third signal terminal 22c, the positive electrode terminal 22d and the negative electrode terminal 22e. It is also possible to provide a connector housing which houses the first signal terminal 22a, the second signal terminal 22b and the third signal terminal 22c, and a connector housing which houses the positive electrode terminal 22d and the negative electrode terminal 22e.

In the above embodiment, the gel member 30 includes first gel member 31, the second gel member 32 and the third gel member 33 which are independently provided. However, the gel member 30 may be a single gel member which collectively covers the first detection electrode 12a, the second detection electrode 12b and the third detection electrode 12c.

In the above embodiment, the gel member 60 includes first gel member 61, the second gel member 62 and the third gel member 63 which are independently provided. However, the gel member 60 may be a single gel member which collectively covers the first detection electrode 52a, the second detection electrode 52b and the third detection electrode 52c.

What is claimed is:

1. A pad for detecting biopotentials comprising:
a first support having a first surface and a second surface;
first electrodes exposed on the first surface;
first terminals exposed on the second surface and electrically connected to the first electrodes;
a secondary battery supported inside the first support;
a charging circuit that is electrically connected to the secondary battery through wiring provided inside the first support, and is supported in the first support and for charging the secondary battery; and
second terminals exposed on the second surface and electrically connected to the secondary battery,
wherein first gel members covering the first electrodes are attachable/detachable to/from the first surface,
a signal processing device having a connecting part is attachable/detachable to/from the second surface, and
when the signal processing device is attached to the second surface, the first terminals and the second terminals are connected to the connecting part.

2. The pad for detecting biopotentials according to claim 1,
wherein the secondary battery and the charging circuit are configured so as to be wirelessly charged.

3. The pad for detecting biopotentials according to claim 1, further comprising:
a second support having a third surface and a fourth surface;
second electrodes;
second gel members covering the second electrodes on the third surface;
fifth terminals exposed on the fourth surface and electrically connected to the second electrodes;
a primary battery supported inside the second support; and
sixth terminals exposed on the fourth surface and electrically connected to the primary battery,
wherein the signal processing device is attachable/detachable to/from the fourth surface, and
wherein when the signal processing device is attached to the fourth surface, the fifth terminals and the sixth terminals are connected to the connecting part.

4. The pad for detecting biopotentials according to claim 1, wherein the secondary battery and the charging circuit are disposed so as to sandwich the first terminals and the second terminals in a top-down view.

5. A biopotential detector comprising:
a first support having a first surface and a second surface;
first electrodes exposed on the first surface;
first terminals exposed on the second surface and electrically connected to the first electrodes;
a secondary battery supported inside the first support;
a charging circuit that is electrically connected to the secondary battery through wiring provided inside the first support, and is supported in the first support and for charging the secondary battery;
second terminals exposed on the second surface and electrically connected to the secondary battery;
gel members that are attachable/detachable to/from the first surface so as to cover the first electrodes; and
a signal processing device that is attachable/detachable to/from the second surface,
wherein the signal processing device includes
a connecting part connected to the first terminals and the second terminals, and
a signal processing circuit configured to process biopotential signals inputted from the connecting part.

6. The biopotential detector according to claim 5,
wherein the signal processing circuit includes a wireless transmission circuit.

7. The biopotential detector according to claim 5,
wherein the signal processing circuit includes a memory that is configured to store data corresponding to the biopotential signals.

8. The biopotential detector according to claim 5,
wherein the signal processing circuit includes a memory that is configured to store information for specifying a subject to which the first support is attached.

9. The biopotential detector according to claim 8, wherein the signal processing circuit includes a receiving circuit configured to receive the information wirelessly.

10. The biopotential detector according to claim 3, further comprising:
a second support having a third surface and a fourth surface;
second electrodes;
second gel members covering the second electrodes on the third surface;
fifth terminals exposed on the fourth surface and electrically connected to the second electrodes;
a primary battery supported in the second support; and
sixth terminals exposed on the fourth surface and electrically connected to the primary battery,
wherein the signal processing device is attachable/detachable to/from the fourth surface, and
when the signal processing device is attached to the fourth surface, the fifth terminals and the sixth terminals are connected to the connecting part.

11. The biopotential detector according to claim 5, further comprising:
a second support having a third surface and a fourth surface;
second electrodes; and
fifth terminals exposed on the fourth surface and electrically connected to the second electrodes.

* * * * *